(12) United States Patent
Kalugin et al.

(10) Patent No.: US 11,262,353 B1
(45) Date of Patent: Mar. 1, 2022

(54) HYBRID MATERIALS FOR BIOCHEMICAL APPLICATIONS

(71) Applicants: Nikolai Kalugin, Albuquerque, NM (US); Alexey Serov, Albuquerque, NM (US); Lindsay Candelaria, Albuquerque, NM (US); Peter Kalugin, Albuquerque, NM (US)

(72) Inventors: Nikolai Kalugin, Albuquerque, NM (US); Alexey Serov, Albuquerque, NM (US); Lindsay Candelaria, Albuquerque, NM (US); Peter Kalugin, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 0 days.

(21) Appl. No.: 16/946,033

(22) Filed: Jun. 3, 2020

Related U.S. Application Data

(60) Provisional application No. 62/856,589, filed on Jun. 3, 2019.

(51) Int. Cl.
    *G01N 33/543* (2006.01)
    *C07K 1/04* (2006.01)

(52) U.S. Cl.
    CPC ....... *G01N 33/54353* (2013.01); *C07K 1/042* (2013.01)

(58) Field of Classification Search
    CPC ............................................... G01N 33/54353
    USPC .......................................................... 549/456
    See application file for complete search history.

(56) References Cited

U.S. PATENT DOCUMENTS 10,826,109 B2 * 11/2020 Serov ................ H01M 10/0525
10,864,460 B2 * 12/2020 Serov ................ B01J 20/28014

* cited by examiner

*Primary Examiner* — Taofiq A Solola
(74) *Attorney, Agent, or Firm* — Gonzales Patent Services; Ellen M. Gonzales

(57) ABSTRACT

Materials and methods for the design of hybrid materials comprising a conducting matrix, organic modifiers/linkers and modifying molecules.

20 Claims, 14 Drawing Sheets

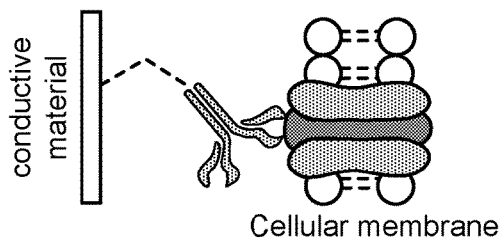
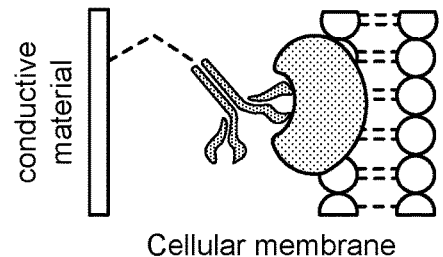
FIG. 13     FIG. 14
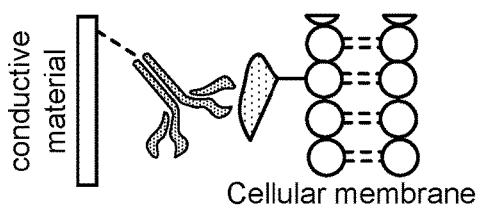
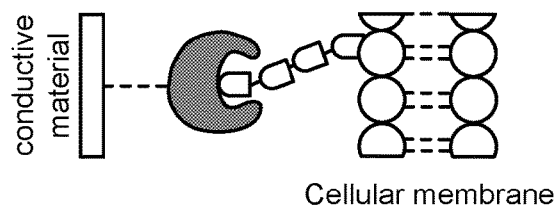
FIG. 15     FIG. 16
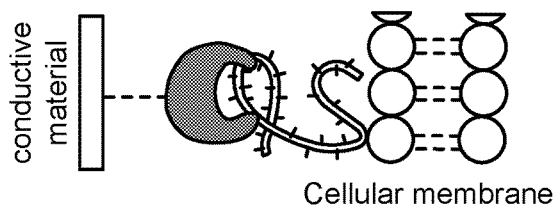
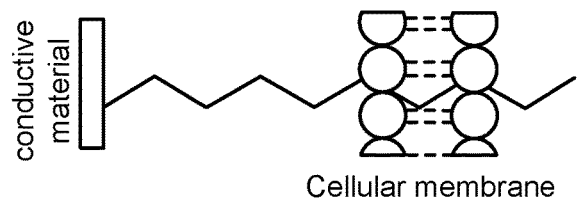
FIG. 17     FIG. 18

- Synthesis (coupling) of amino acids was specific to Ha-tag sequence
- Aspartic Acid residues contained OMpe protecting groups
- Tyrosine residues contain -tBu protecting groups
- Glycine (4) residues were added initially to extend overall length of the available Ha-tag chain

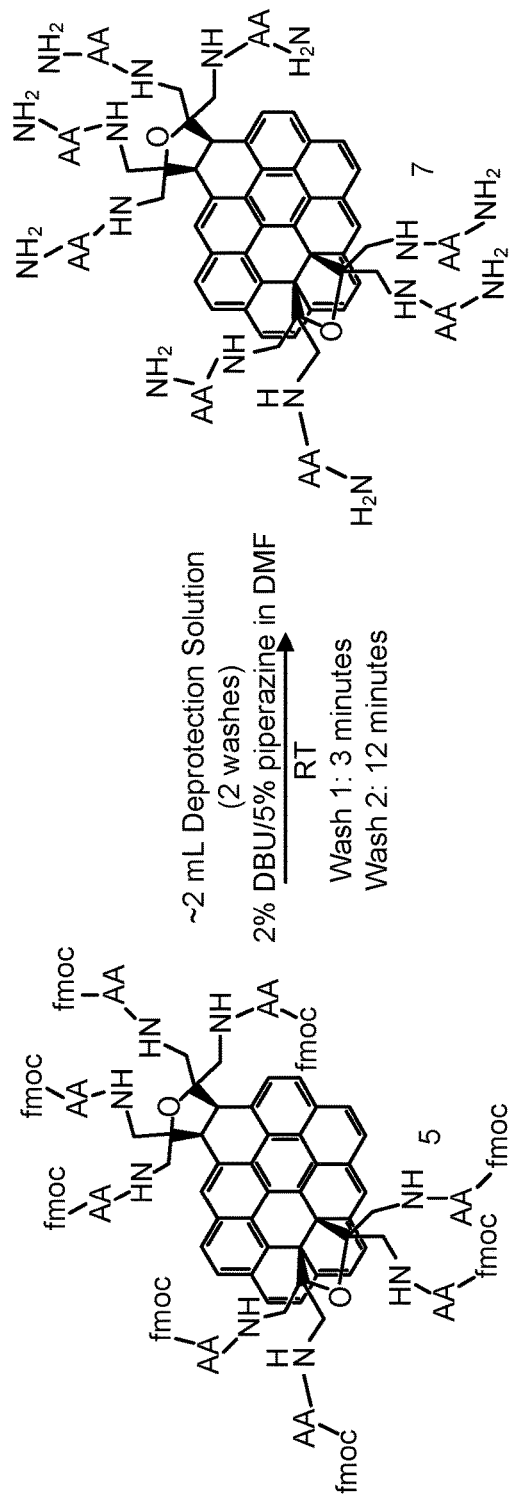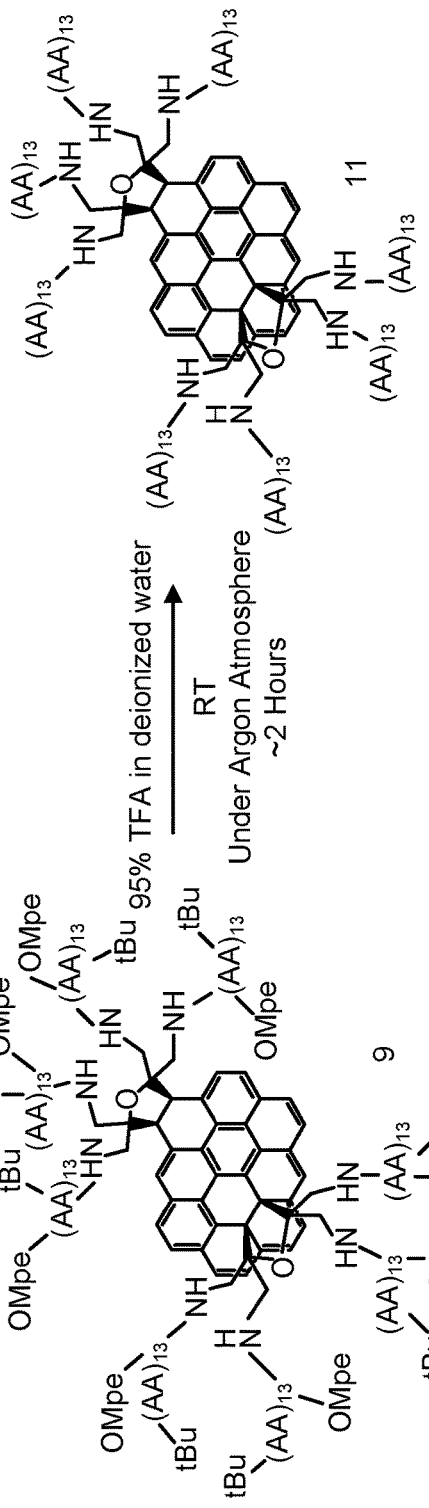
FIG. 25
FIG. 26
AA- Amino Acid

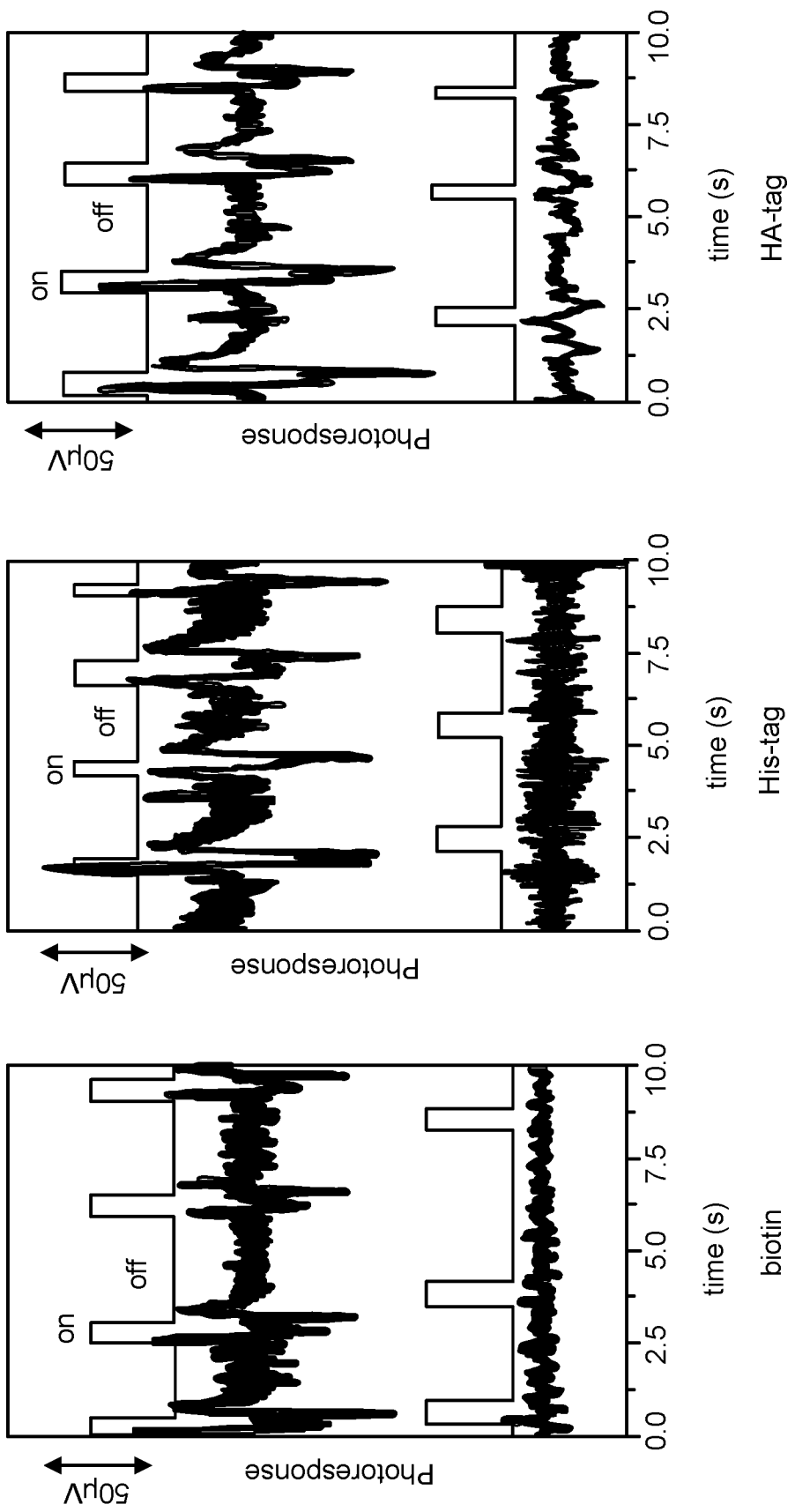

HYBRID MATERIALS FOR BIOCHEMICAL APPLICATIONS

CROSS-REFERENCE TO RELATED APPLICATIONS

The following application claims benefit of U.S. Provisional Application No. 62/856,589 filed Jun. 3, 2019, which is hereby incorporated by reference in its entirety.

BACKGROUND

The induction and detection of stimuli in electrically active cells in living tissues, most commonly neurons and myocytes, is a crucial tool in the study of such cells. The methods used for these purposes involve a combination of optical, genetic, and electronic techniques. Such methods have limitations in the usage of light-sensitive proteins, optogenetic actuators, and/or metallic electrodes. Accordingly, there is a need for organic, biofunctionalized, fully molecularly-defined materials that can be used as electrodes for a variety of applications including, but not limited to, neuronal interfaces. Of particular need are materials that address some of the fundamental problems of electrophysiology related to tissue disruption and toxicity, stability of long-term contacts, and signal quality and specificity.

SUMMARY

According to various embodiments, the present disclosure provides materials and methods for the design of hybrid materials comprising a conductive matrix, organic modifiers/linkers and modifying molecules for application in genetics, catalysis, separation, optical and opto-electronic devices, drug delivery, sensors, energy conversion, et al. The particular applications may include electrodes to living cells, affinity chromatography, scaffolding for tissue engineering, substrates for Solid Phase Peptide Synthesis, self-organized fabrication of electronic and optoelectronic devices and materials, biomolecular sensors, electronic (non-optical) DNA sequencing, et. al.

Accordingly, described herein is the usage of a conductive matrix modified with neutral or charged organic/inorganic linkers, which can be attached to the surface of the conductive matrix via covalent bonding, physisorption, chemisorption, grafting, through additional molecules etc. In general, these organic molecules can then be used as docking centers for modifying molecules. The overall hybrid material allows the delivery of an electric field to the final target with control of field strength, field pulse time, penetration depth etc.

BRIEF DESCRIPTION OF THE DRAWINGS

FIG. 13 is a schematic illustration of a hybrid material of the present disclosure which presents surface-bound antibodies as a method for attachment to transmembrane peptides.

FIG. 14 is a schematic illustration of a hybrid material of the present disclosure which presents surface-bound antibodies as a method for attachment to intramembrane proteins.

FIG. 15 is a schematic illustration of a hybrid material of the present disclosure which presents surface-bound antibodies as a method for attachment to membrane-associated proteins.

FIG. 16 is a schematic illustration of a hybrid material of the present disclosure which presents surface-bound adhesive proteins as a method for attachment to membrane phospholipid tails.

FIG. 17 is a schematic illustration of a hybrid material of the present disclosure which presents surface-bound adhesive proteins as a method for attachment to extracellular matrix (ECM) components.

FIG. 18 is a schematic illustration of a hybrid material of the present disclosure which presents lipids capable of adhering to and directly spanning the plasma membrane.

FIG. 25 depicts the chemical process of Fmoc deprotection of the terminal monomer.

FIG. 26 depicts the chemical process of final side chain deprotection.

FIG. 33 shows the results of photoinduced electrical potential traces obtained with irradiation by a broad-spectrum quartz-halogen lamp for His-tag-functionalized graphite incubated with His-tag antibody-coated quantum dots (red) and streptavidin-coated quantum dots (olive).

FIGS. 34 and 35 show the results of photoinduced electrical potential traces obtained with irradiation by a broad-spectrum quartz-halogen lamp for HA-tag-functionalized graphite incubated with fluorophore-coated HA-tag antibodies (red) and His-tag antibody-coated quantum dots (olive). Photoresponse is evident when binders and surface modifications are paired correctly, while minimal to no signal is detected in mismatched surface-binder pairs. The corresponding type of graphite functionalization is indicated in italics.

DETAILED DESCRIPTION

According to an embodiment, the present disclosure provides novel hybrid materials comprising a conductive matrix, organic or inorganic modifiers/linkers and modifying molecules and methods for making and using the same. These materials can be used to modify or detect local electric fields, interfacing with cellular membrane potentials and monitoring or controlling them. The materials can also be functionalized with bioactive molecules and proteins to interact directly with cellular proteins in a nontoxic manner. Other applications of the invented materials include affinity chromatography, scaffolding for tissue engineering, substrates for Solid Phase Peptide Synthesis (SPPS), self-organized fabrication of electronic and optoelectronic devices and materials, biomolecular sensors, electronic (non-optical) DNA sequencing, and others.

In general, the novel hybrid materials of the present disclosure comprise a conductive matrix formed from or including modified (or functionalized) carbon. For ease of description, the term "carbon" is used herein to refer to both graphite and graphene. Moreover, while the descriptions herein are directed primarily to flat carbon surfaces (i.e. graphite or graphene sheets), the presently described methods can also be applied to both flat and curved or other "non-flat" carbon shapes including, but not limited to, fullerenes such as carbon nanotubes (CNTs), and buckyballs, as well as other form of sp2-bonded carbon including, but not limited to, mesoporous carbon, 3D graphene nanosheets, other forms of nonplanar graphite exhibiting arched edges, polyhedral crystals, whiskers, cones, and other geometries.

In general, the carbon surface is functionalized to enable decoration with a variety of biological or non-biological entities. Importantly, unlike previously described graphite/graphene functionalization methods which modify or functionalize only the edges of the graphite/graphene (typically in the form of graphene oxide), the present disclosure provides mechanisms for functionalization of pristine graphene at internal molecular sites making the entire surface of the conducting matrix available for further attachment chemistry. For ease of reference, the term "modified carbon" or "modified carbon support" is used herein to refer to a carbon structure which has been modified to present internal molecular sites available for further attachment chemistry across the entire surface of the carbon structure.

Figure 1:
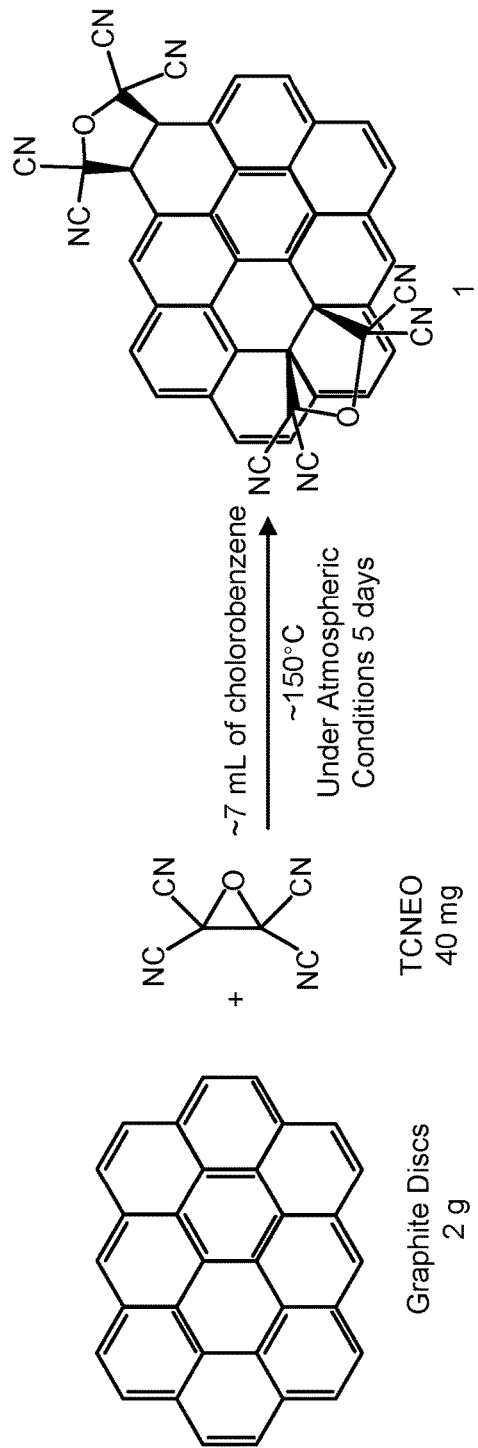
FIG. 1 depicts the chemical process of attaching tetracyanoethylene oxide (TCNEO) to carbon.
Figure 2:
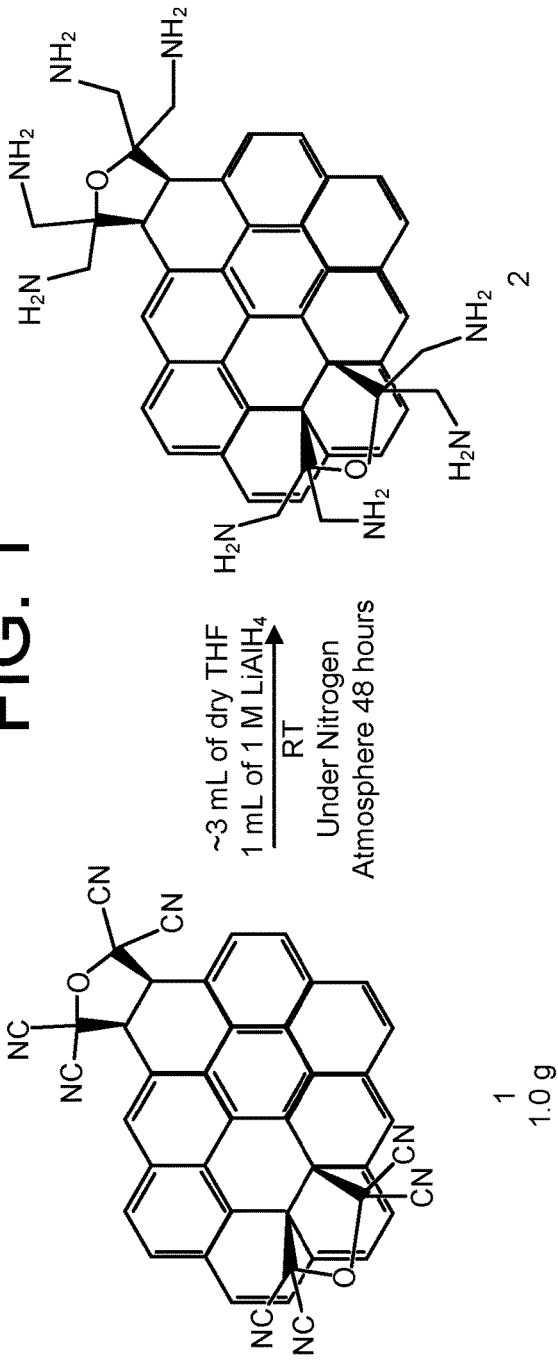
FIG. 2 depicts the reduction of the TCNEO-modified carbon to produce the reactive nitrile groups.

According to a specific embodiment, the carbon surface is modified via a tetracyanoethylene oxide (TCNEO)-based technique, which results in decoration of the carbon surface with reactive nitrile groups. According to a specific embodiment, TCNEO modification comprises attaching TCNEO to carbon (FIG. 1) followed by reduction of the TCNEO-modified carbon to produce the reactive nitrile groups (FIG. 2). Additional details regarding an exemplary TCNEO modification are provided below in the Examples section. See also Candelaria, L., Frolova, L. V., Kowalski, B. et al. Surface-modified three-dimensional graphene nanosheets as a stationary phase for chromatographic separation of chiral drugs. *Sci Rep* 8, 14747 (2018). https://doi.org/10.1038/s41598-018-33075-w, which is hereby incorporated by reference for all purposes.

According to another embodiment, the carbon surface, particularly if it is curved, may be modified using an azomethine ylide attachment method as described in Cao and Houk, J. Mater. Chem., 2011, 21, 1503-1508, which is incorporated by reference for all purposes.

Figure 3:
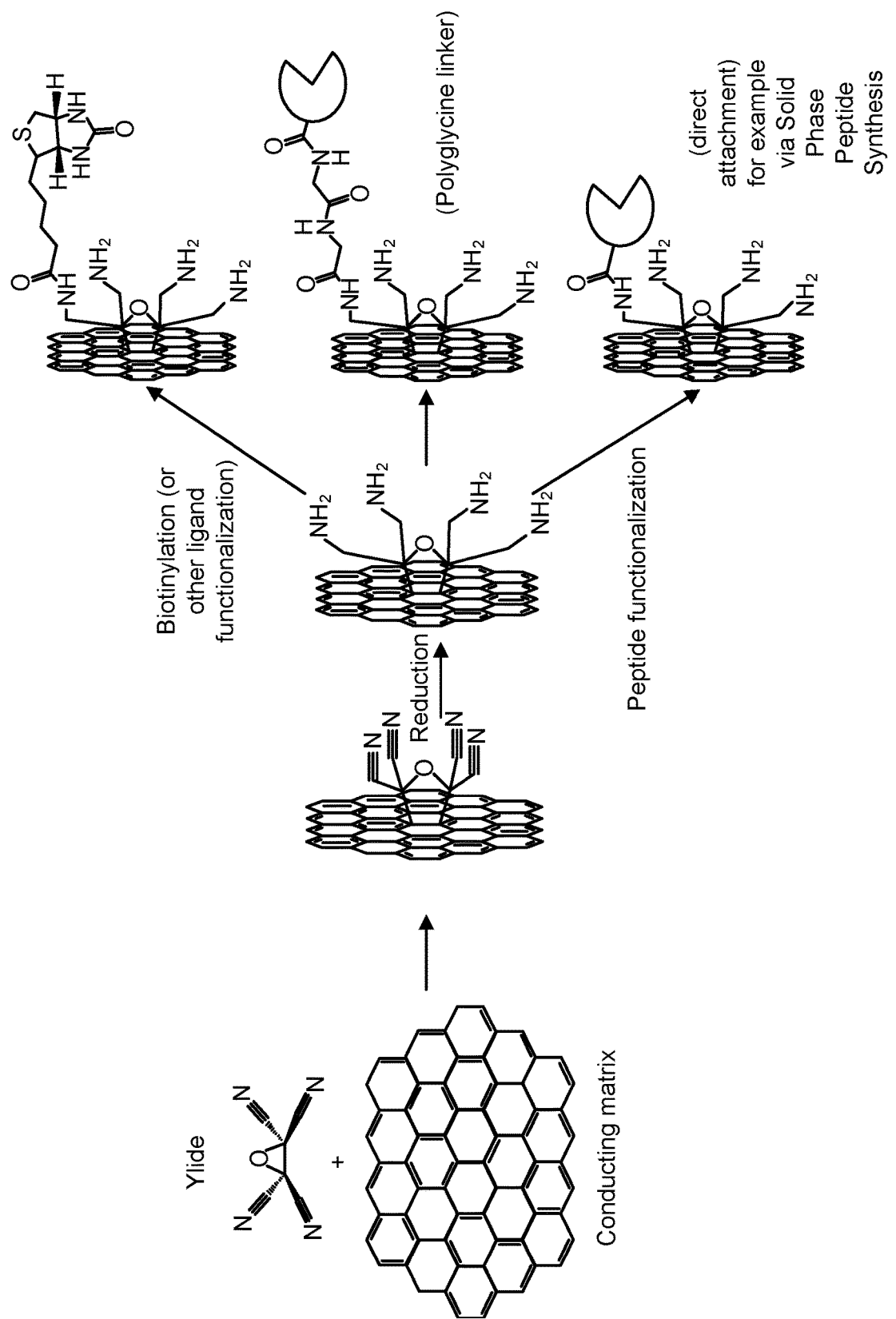
FIG. 3 is a schematic illustration of the steps of modifying carbon to produce the hybrid materials of the present disclosure.

According to various embodiments, and as shown in FIG. 3, the modified carbon can then be decorated with any number of entities including, for example, aminoacids, peptides, polypeptides, polymers, proteins, lipids, nucleic acids, and other molecules of a range of complexities. While several specific examples are provided herein and in the Examples section below, it will be understood that the presently described methods and materials can be used in a nearly limitless number of applications and that such possibilities are contemplated by the present disclosure.

According to various embodiments, the modified carbon may be decorated with linker molecules to enable attachment to a wide variety of binding proteins. As non-limiting examples, and as demonstrated in the Examples section below, the modified carbon may be decorated with biotin, His-tags, HA-tags, or the like.

Figure 4:
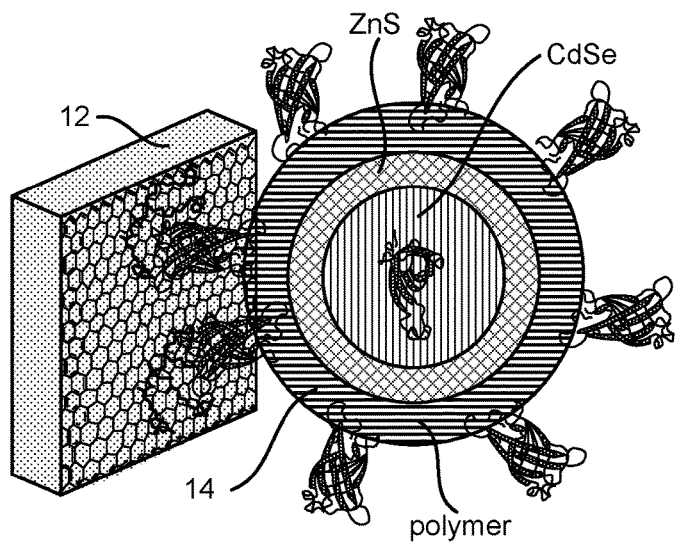
FIG. 4 is a schematic representation of a biotin-functionalized modified graphite surface of the present disclosure showing the associated streptavidin-coated quantum dot.
Figure 5:
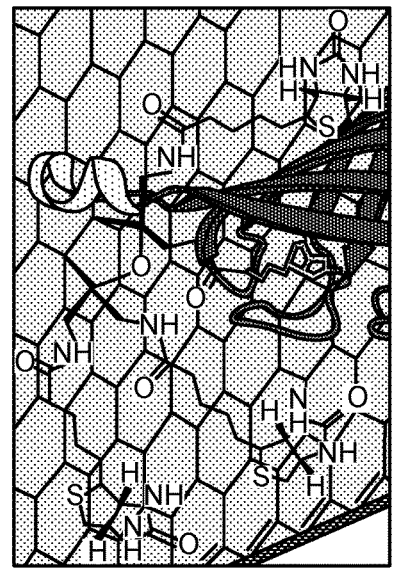
FIG. 5 shows the molecular details of the graphite surface attachment in FIG. 4.

FIG. 4 is a schematic representation of a biotin-functionalized modified graphite surface 12 of the present disclosure showing the associated streptavidin-coated quantum dot 14. FIG. 5 shows the molecular details of the graphite surface attachment in FIG. 4.

Figure 6:
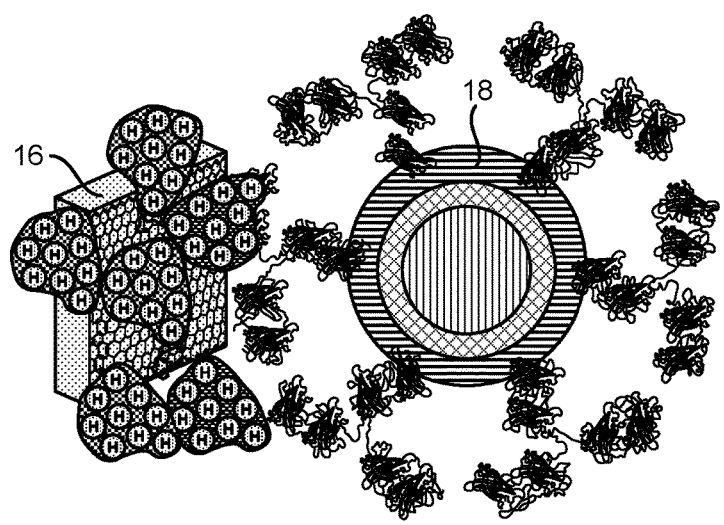
FIG. 6 is a schematic representation of a His-tag-functionalized modified graphite surface of the present disclosure with an associated His-tag antibody-coated quantum dot.
Figure 7:
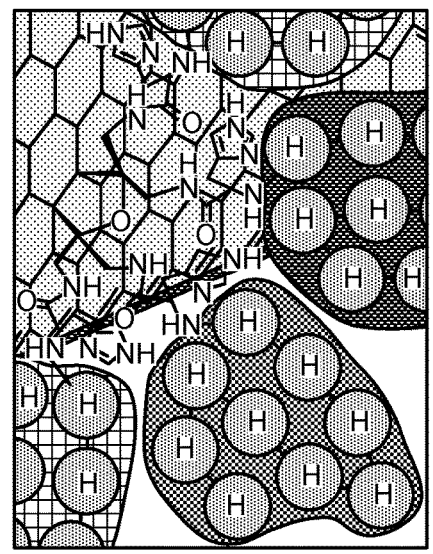
FIG. 7 shows the molecular details of the graphite surface attachment in FIG. 6 including the attached histidine amino acids ("H").

FIG. 6 is a schematic representation of a His-tag-functionalized modified graphite surface 16 of the present disclosure with an associated His-tag antibody-coated quantum dot 18. FIG. 7 shows the molecular details of the graphite surface attachment in FIG. 6 including the attached histidine amino acids ("H").

Figure 9:
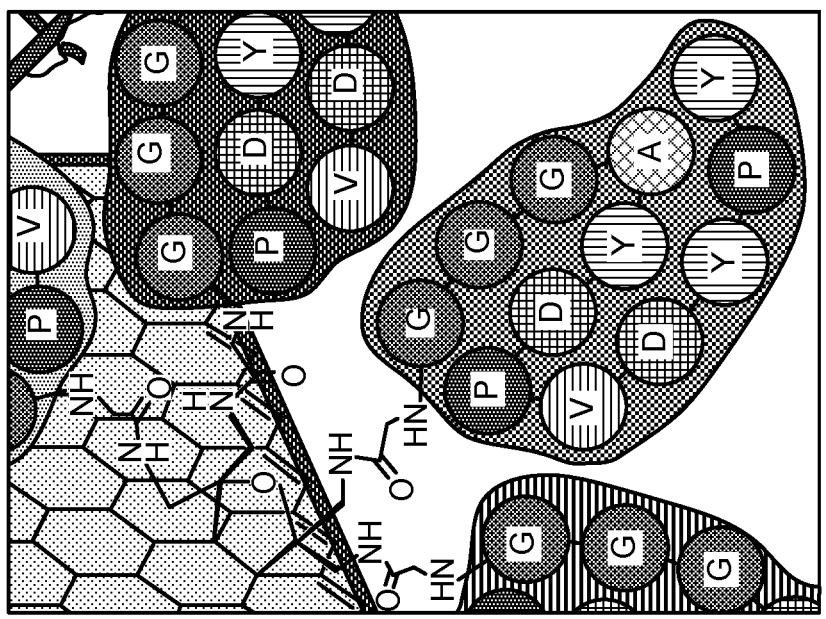
FIG. 9 shows the molecular details of the graphite surface attachment in FIG. 8 including the attached amino acids.
Figure 8:
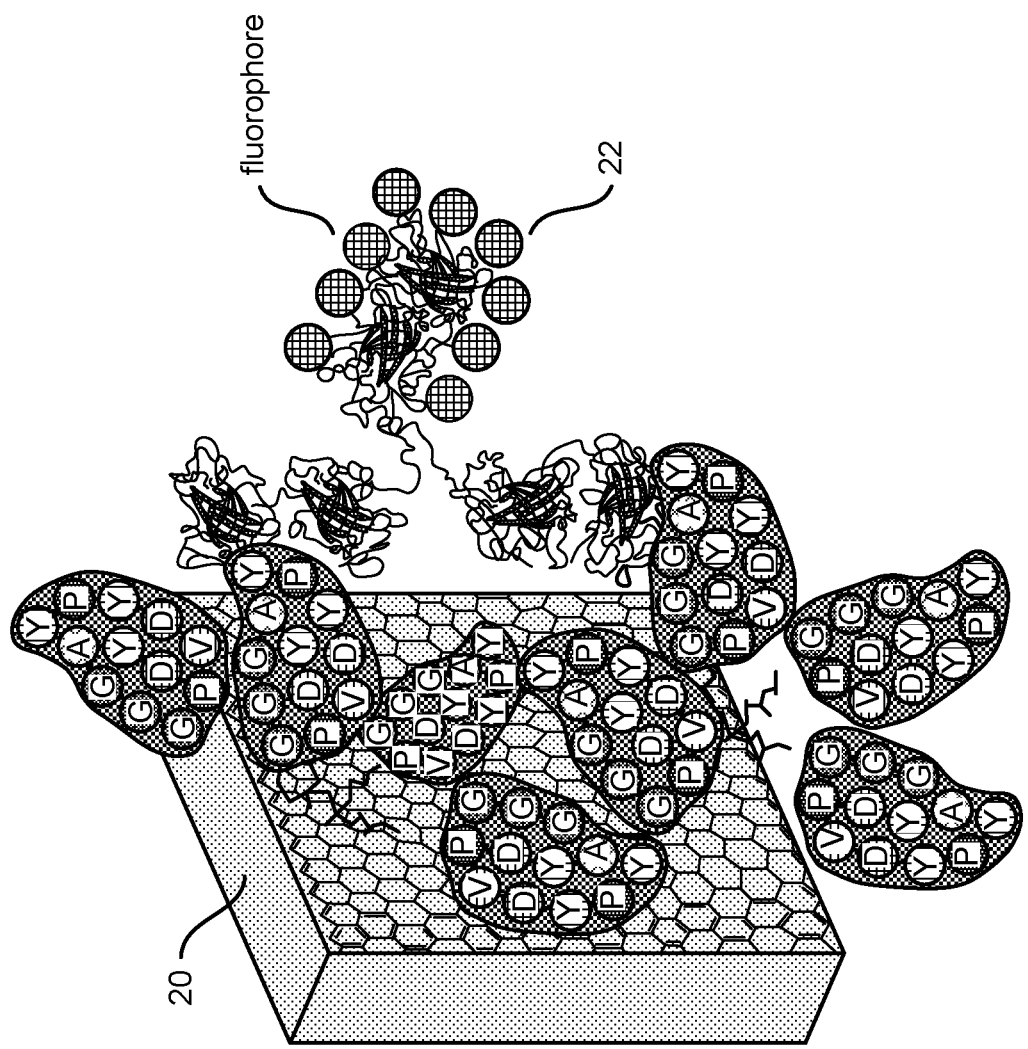
FIG. 8 is a schematic representation of a HA-tag functionalized modified graphite surface of the present disclosure with an associated fluorophore-coated HA tag antibody.

FIG. 8 is a schematic representation of a HA-tag functionalized modified graphite surface 20 of the present disclosure with an associated fluorophore-coated HA tag antibody 22. FIG. 9 shows the molecular details of the graphite surface attachment in FIG. 8 including the attached glycine ("G"), alanine ("A"), tyrosine ("Y"), aspartic acid ("D"), proline ("P") and valine ("V") amino acids.

According to various embodiments, and as demonstrated in the Examples section below, the modified carbon may be used as a support for solid phase peptide synthesis (SPPS). The ability to use the modified carbon as a support for SPPS opens up the possibilities for the production and use of a nearly unlimited number of hybrid materials as any desired peptide can be custom assembled on the carbon-based support.

According to further embodiments, the modified carbon of the present disclosure can be decorated using covalent modification strategies such as click chemistry to attach preformed peptides, proteins, lipids, nucleic acids, and the like.

According to various embodiments, the modified carbon of the present disclosure may incorporate photolithographic or other techniques commonly used in DNA microarray technology to create precise spatial patterning or other alterations.

For ease of discussion, the term "hybrid material" is used herein to describe a modified carbon support decorated with either organic or inorganic biological materials.

Figure 10:
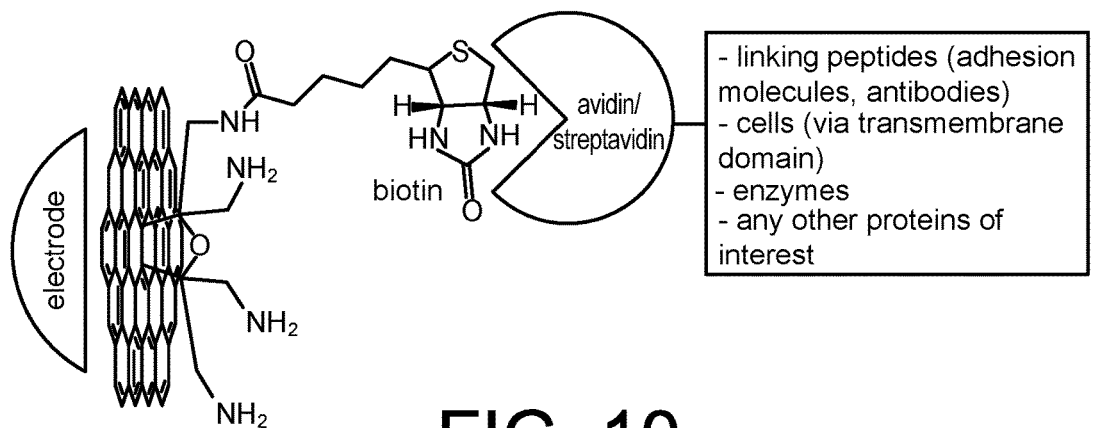
FIG. 10 is a schematic illustration of an electrode according to an embodiment of the present disclosure.
Figure 11:
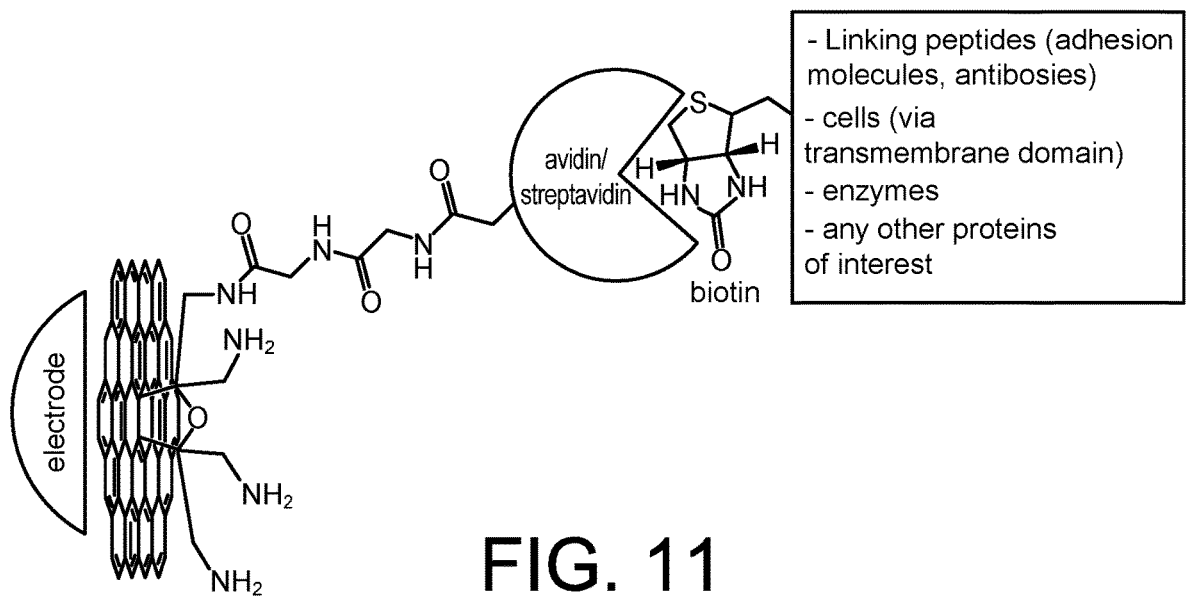
FIG. 11 is a schematic illustration of an electrode according to another embodiment of the present disclosure.
Figure 12:
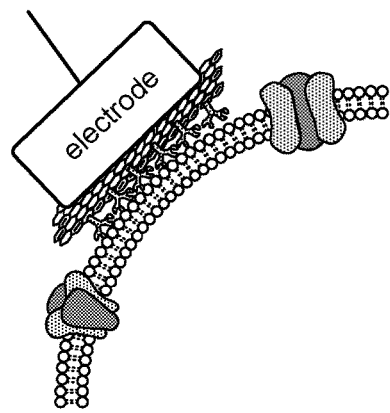
FIG. 12 is a schematic illustration of an electrode according to an embodiment of the present disclosure attached to a membrane.

According to various embodiments, and as shown in FIGS. 10-12, the hybrid materials of the present disclosure can be used for a variety of applications including, but not limited to, as biocompatible electrodes for biological applications. The hybrid materials of the present disclosure are particularly well suited for use as biocompatible electrodes in that they can be designed to include linkers (tags, antibodies, antigens, etc.) that direct and attach the electrode to a specific cell, location, and/or position, as well as bioactive moieties to act as signals to be recognized by the immune system and the local tissue environment. In FIG. 10, the electrode comprises the hybrid material with an attached biotin molecule, which can then bind with avadin/streptavidin for use in, for example, an affinity assay. In FIG. 11, the electrode comprises the hybrid material with an attached avadin/streptavidin molecule which can then bind with a biotin molecule for use in, for example, an affinity assay. FIG. 12 shows the electrode attached to a membrane.

FIGS. 13-18 depict various exemplary surface modifications to produce hybrid materials suitable for direct neuronal interfaces/adhesion. Of course, it will be understood that such hybrid materials are suitable for a wide variety of other applications as well. FIG. 13 shows antibodies attached to transmembrane peptides. FIG. 14 shows antibodies attached to intramembrane proteins. FIG. 15 shows antibodies attached to membrane-associated proteins. FIG. 16 shows adhesive proteins attached to membrane phospholipid tails. FIG. 17 shows adhesive proteins attached to extracellular matrix (ECM) components. FIG. 18 shows lipids capable of adhering to and spanning the plasma membrane directly.

Unlike current biological electrodes which are frequently formed from metals like platinum, which can be reactive and even harmful under certain biological conditions, carbon is generally biologically inert making it safer and less likely (or unlikely) to interfere in any biological process. Such biocompatible electrodes also be could be used in graphene-based DNA sequencing technologies, as biomolecular sensors, and as surfaces and/or scaffolds that display particular bioactive signals to interface with cultured or in vivo cells and specifically influence their behavior.

Figure 19:
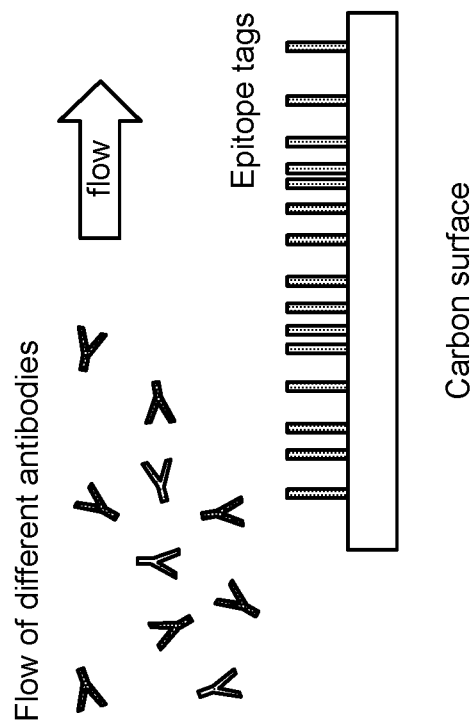
FIG. 19 is a schematic illustration of a chromatography assay using the hybrid materials of the present disclosure.
Figure 19:
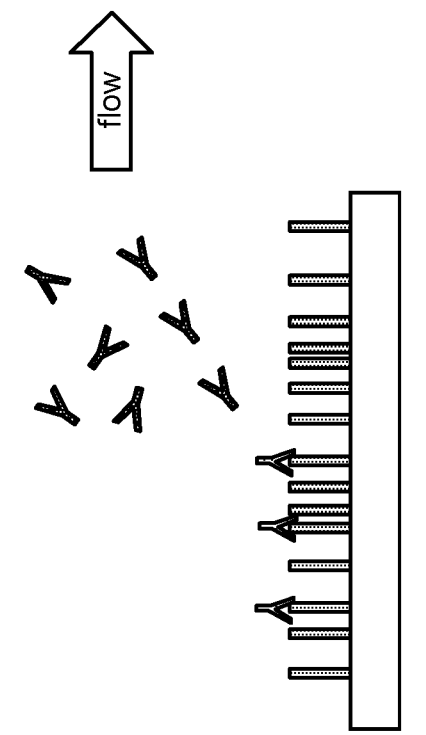

According to another embodiment, the hybrid materials of the present disclosure can be used in chromatography applications, as illustrated in FIG. 19. As shown, the carbon surface can be modified to include epitope tags which are designed to capture desired antibodies, allowing non-desired antibodies and other entities to flow through.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

REFERENCES

Candelaria, L., Kalugin, P. N., Kowalski, B. M. et al. Covalent Epitope Decoration of Carbon Electrodes using Solid Phase Peptide Synthesis. *Sci Rep* 9, 17805 (2019). https://doi.org/10.1038/s41598-019-54000-9

Examples and Experiments

Graphite Surface Modification

TCNEO attachment and reduction—2 g of graphite discs and 40 mg of TCNEO were mixed in 7 mL chlorobenzene and refluxed at 150° C. for 5 days under atmospheric conditions. The mixture was also stirred from 24 hours after reaction start until its completion. The sample mixture was then filtered off, and the functionalized graphite was washed 3× with acetone, 3× with methanol, 3× with acetonitrile, and 3× with acetone. Sample 1 was dried at room temperature (RT) overnight (FIG. 1). Next, 1.0 g dry 1 was added to 3 mL dry THF. Under inert conditions ($N_2$), 1 mL of 1 M $LiAlH_4$ in diethyl ether was then added dropwise over 6 minutes. The reaction was stirred and proceeded at RT for 48 hours. After reaction completion, aqueous workup was performed, and the sample mixture was filtered off. The sample was neutralized to pH 7 and washed 3× with acetone, 3× with methanol, and 3× with acetone. Sample 2 was dried at RT overnight (FIG. 2).

Figure 20:
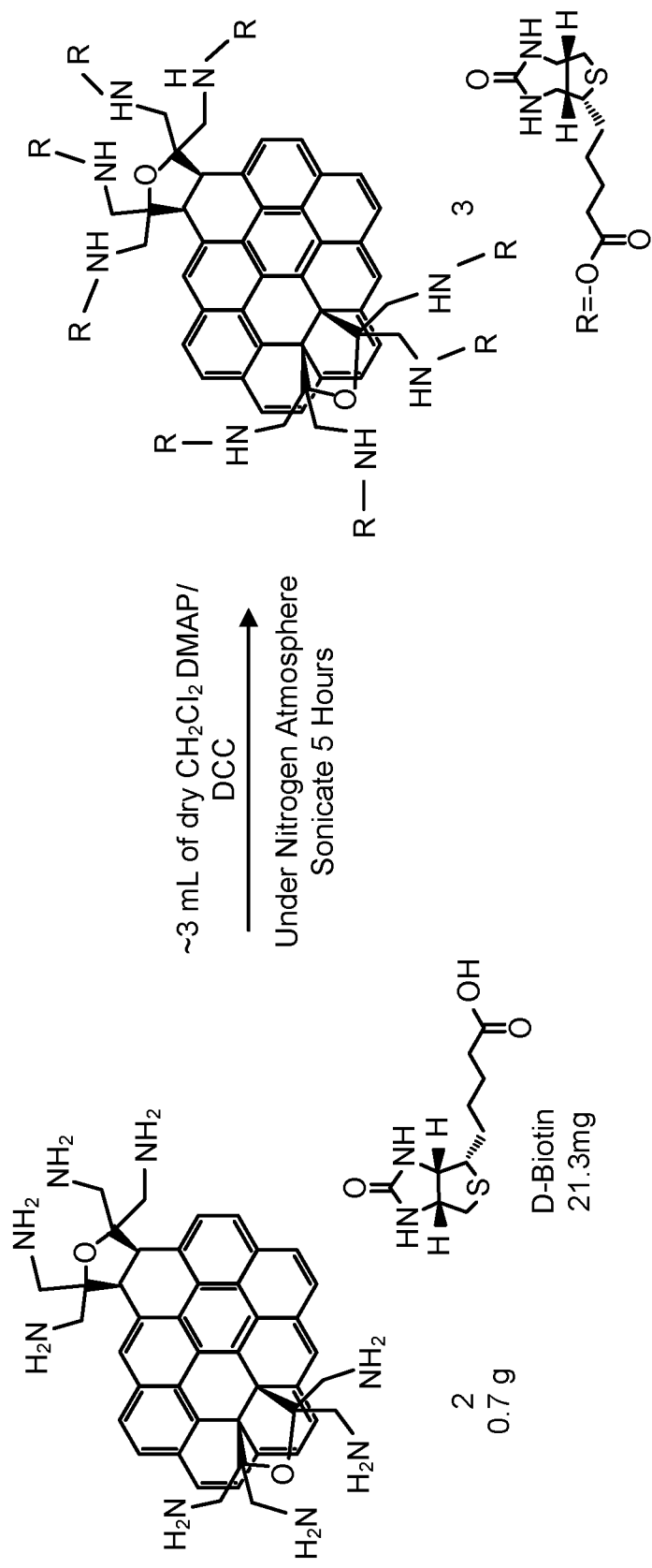
FIG. 20 depicts the chemical process of biotinylation of TCNEO-modified graphite.

Biotinylation of TCNEO-Modified Graphite 0.7 g dry 2, 21.3 mg (8.73e-5 mmol) D-(+)-biotin, 24.0 mg (1.16e-4 mmol) DCC, and catalytic 5 mg (4.09e-5 mmol) DMAP were added to 3 mL dry dichloromethane under inert conditions ($N_2$) and sonicated for 5 hours at RT. The sample was then washed 1× with $dH_2O$, 3× with acetone, 3× with methanol, and 3× with acetone. Sample 3 was dried at RT overnight (FIG. 20).

Solid Phase Peptide Synthesis on TCNEO-Modified Graphite

Solid phase peptide synthesis (SPPS) was implemented to attach His- and HA-tags to reduced TCNEO-modified graphite 2. Fmoc-protected amino acid monomers, with tBu-, Trt- and OMpe-protected side chains, were used. Alternating steps of monomer attachment and Fmoc-deprotection were performed to build the peptide chains, followed by a final deprotection of side chain protecting groups.

Figure 21:
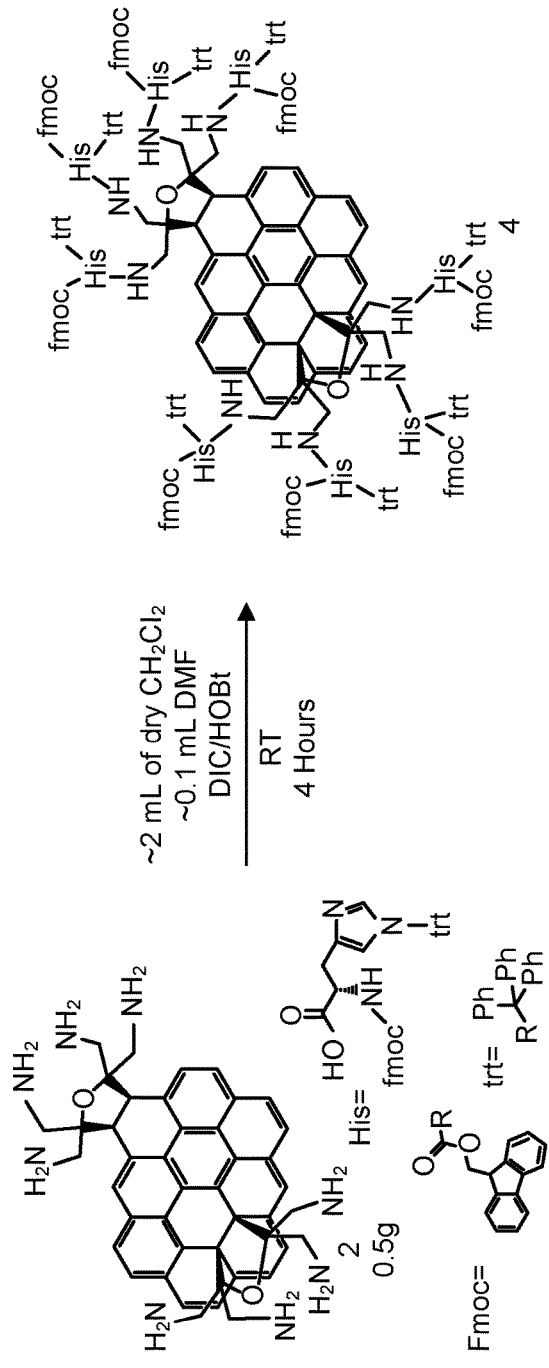
FIG. 21 depicts the chemical process of histidine monomer attachment.
Figure 22:
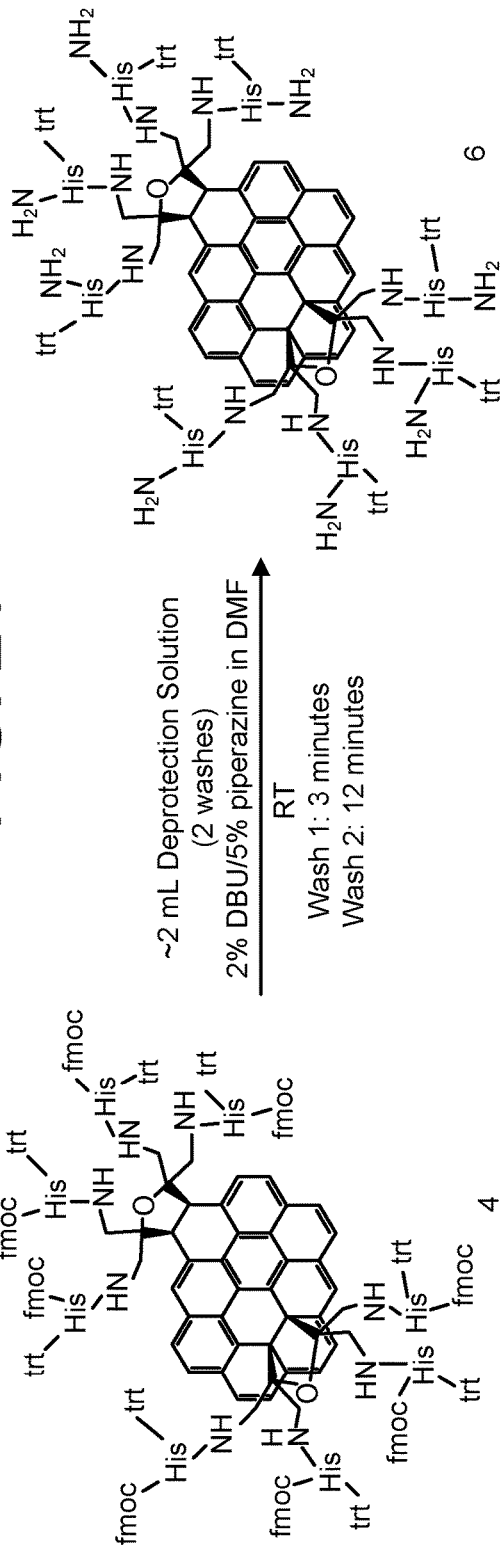
FIG. 22 depicts the chemical process of Fmoc deprotection of the terminal monomer.
Figure 23:
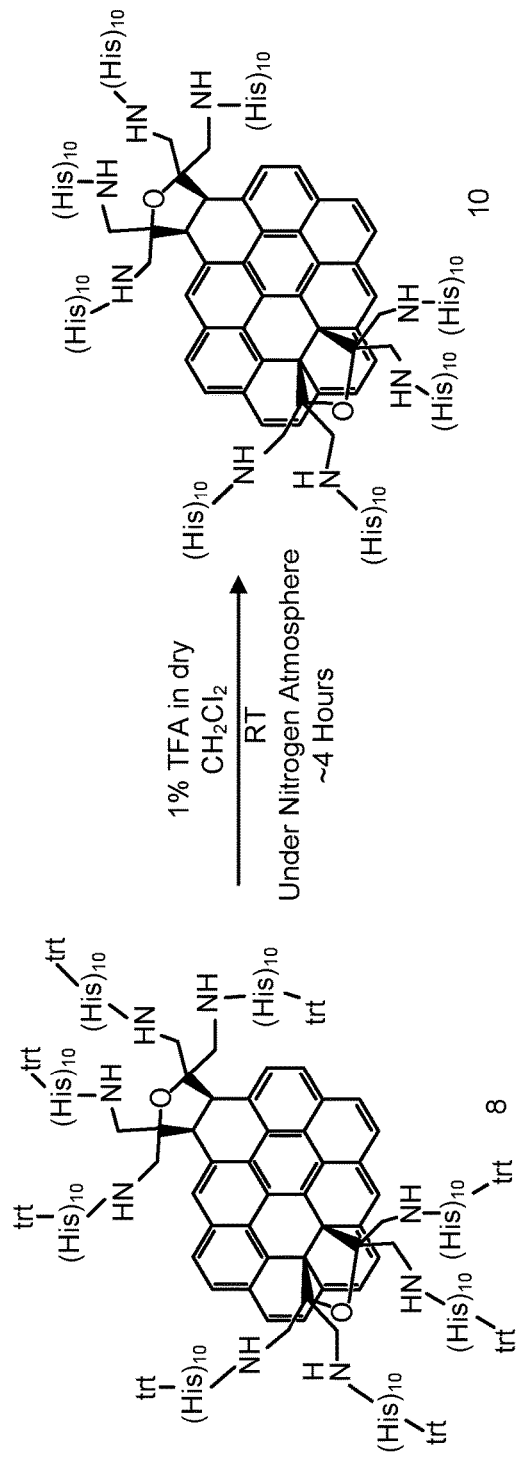
FIG. 23 depicts the chemical process of final side chain deprotection.

FIGS. 21-23 show His-tag attachment. 10 H monomers were attached in a row. FIG. 21 shows the step of histidine monomer attachment. FIG. 22 shows the step of Fmoc deprotection of the terminal monomer. FIG. 23 shows the final side chain deprotection step.

Figure 24:
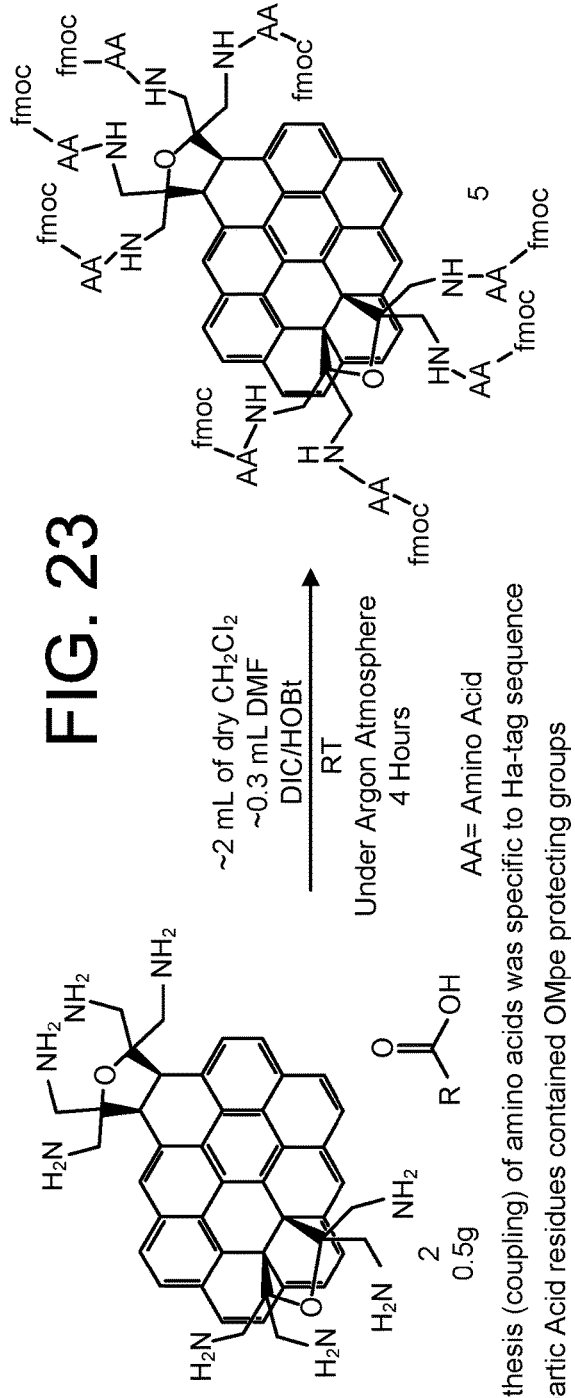
FIG. 24 depicts the chemical process of amino acid monomer attachment.

FIGS. 24-26 show the steps of HA-tag attachment. 13 monomers were attached in the order G-G-G-G-A-Y-D-P-V-D-Y-P-Y, with a 4-glycine linker connecting the epitope tag to the graphite surface (SPPS builds peptide chains in the C-terminus to N-terminus orientation). FIG. 24 shows the step of amino acid monomer attachment. FIG. 25 shows the step of Fmoc deprotection of the terminal monomer. FIG. 26 shows the final side chain deprotection step.

To begin with, 0.5 g dry 2 was added to 1 mL dry dichloromethane under inert conditions (Ar). In a separate flask, 55 mg HOBt and 50 mg of appropriate amino acid monomer were dissolved in 1 mL dry dichloromethane and 0.1-0.3 mL dry DMF (0.1 mL for H, 0.3 mL for all other monomers). The amino acid mixture was added to the sample flask along with 3.5 drops (5.5 equivalents to TCNEO) DIC, and the mixture was stirred for 4 hours at RT. The sample mixture was then filtered off, and the sample was washed 1× with $dH_2O$, 3× with acetone, 3× with methanol, 3× with acetonitrile, and 3× with acetone. The sample 4/5 was dried at RT overnight.

For Fmoc-deprotection, a deprotection solution was made consisting of 8 mL dry DMF with 0.1632 g (2% w/v) DBU and 400 mg (5% w/v) piperazine. Dry sample was placed in 2 mL deprotection solution and shaken vigorously (900 rpm) at RT for 3-5 min (3 min for monomers 1-3 in the chain, 4 min for monomers 4-7, and 5 min for monomers 8-13). The solution was then decanted, another 2 mL was added to the sample, and it was again shaken vigorously (900 rpm) at RT for 12-14 more min (12 min for monomers 1-3, 13 min for monomers 4-7, and 14 min for monomers 8-13). Solution was again decanted, and the sample was then washed with 2 mL deprotection solution and 3× alternating washes of 2 mL dry DMF and 2 mL dry dichloromethane. The sample 6/7 was dried at RT overnight, and then proceeded to next monomer attachment in dichloromethane as above. These two steps were alternated until completion of peptide chains to samples 8/9.

Final deprotection of His-tagged sample with Trt-group removal began with the addition of 8 to 3 mL dry dichloromethane with 0.0447 g (1%) TFA. This mixture was stirred at RT for 4 hours under inert conditions ($N_2$). The sample mixture was then filtered off, and the sample was washed 3× with acetone, 3× with methanol, 3× with acetonitrile, and 3× with acetone. Sample 10 was dried overnight. Final deprotection of HA-tagged sample with tBu- and OMpe-group removal began with the addition of 9 to 3.85 mL (95%) TFA with 0.15 mL $dH_2O$. This mixture was stirred at RT for 2 hours under inert conditions (Ar). The sample mixture was then filtered off, and the sample was washed 3× with acetone, 3× with methanol, 3× with acetonitrile, and 3× with acetone. Sample 11 was dried overnight.

Binding Protein Attachment to Functionalized Graphite

Two buffer solutions were prepared for antibody attachment experiments: blocking buffer (6% BSA/10% normal mouse serum in 1×PBS) and incubation buffer (6% BSA in 1×PBS). All antibody stocks were centrifuged at 5000 g for 3 min prior to use, and aliquots were taken from the supernatant. Antibodies were diluted in incubation buffer at ratio 1:2 for HA-tag Monoclonal Antibody (2-2.2.14) DyLight 550 and 1:10 for WesternDot 655 His-tag Mouse Monoclonal Antibody and Qdot 585 Streptavidin Conjugate. Surface-modified graphite samples were incubated in blocking buffer for 1 hour, then with antibodies in incubation buffer for 1 hour. Afterwards, they were washed 3× with 1×PBS for 5 min each and kept in 1×PBS for spectroscopic and photoresponse measurements. All steps were performed at RT.

Confirmation of Functional Surface Tag Decoration

Figure 27:
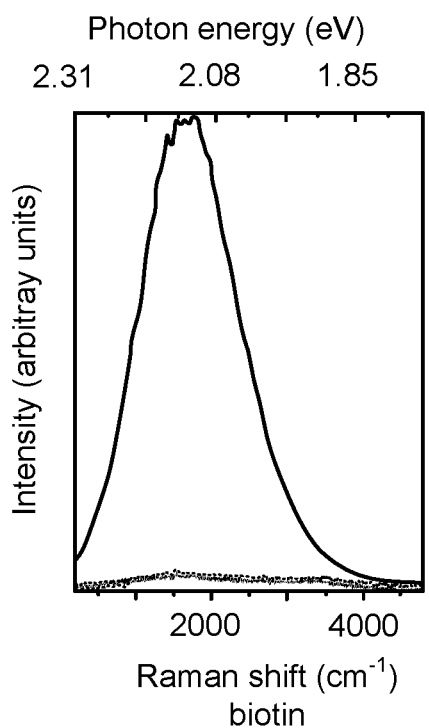
FIG. 27 shows Raman and fluorescence spectra of biotin-functionalized graphite surfaces prior to binding protein treatment (orange), after incubation with streptavidin-coated quantum dots (red), and after incubation with His-tag antibody-coated quantum dots (olive).
Figure 28:
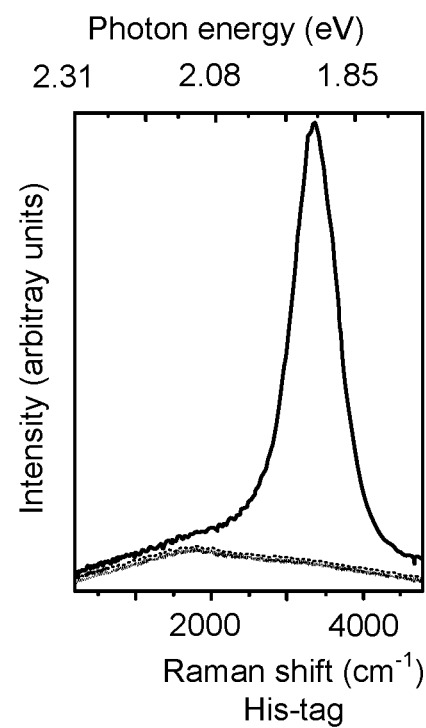
FIG. 28 shows Raman and fluorescence spectra of His-tag-functionalized surfaces prior to binding protein treatment (orange), after incubation with His-tag antibody-coated quantum dots (red), and after incubation with streptavidin-coated quantum dots (olive).
Figure 29:
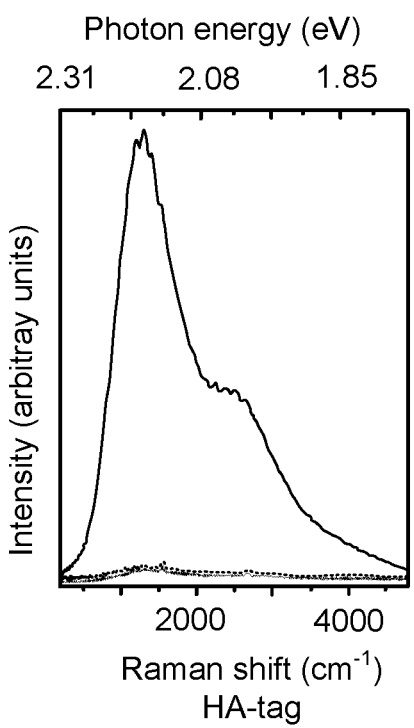
FIG. 29 shows Raman and fluorescence spectra of HA-tag-functionalized surfaces prior to binding protein treatment (orange), after incubation with fluorophore-coated HA-tag antibodies (red), and after incubation with His-tag antibody-coated quantum dots (olive). Note the robust signals in cases of correctly paired surface tags and binding proteins, and absence of signal in mismatched samples.
Figure 30:
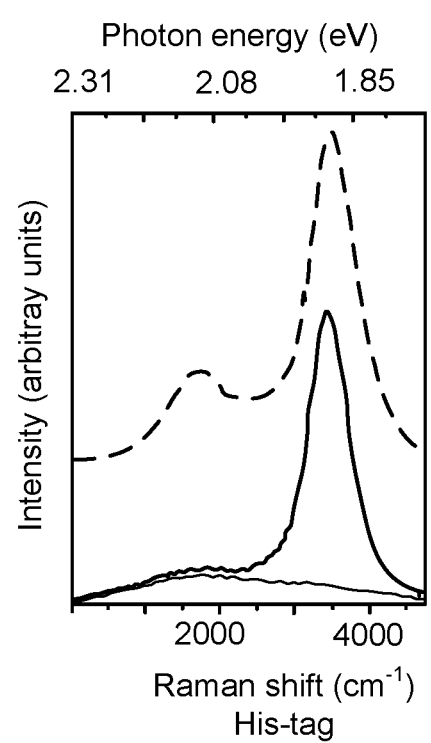
FIG. 30 is a schematic illustration of a cuvette filled with deionized water, containing the labeled surface-tagged graphite and leads connected to the sample and the water for detection of photoinduced electrical potentials near quantum dot surfaces and chemical fluorophores. Light path restricted by Faraday cage is shown.

To confirm the functionality of surface-attached biotin and epitope tags, differential affinity experiments were performed using streptavidin (Qdot 585, 585 nm/2.119 eV emission)- and anti-His-tag antibody (WesternDot 655, 655 nm/1.893 eV emission)-coated CdSe quantum dots in ZnS shells, as well as fluorophore-labeled anti-HA-tag antibodies (DyLight 550, 576 nm/2.152 eV emission). First, surface-tagged graphite samples were incubated with solutions of individual labels and assessed for retention of appropriate binders after washing by measurement of their fluorescence/Raman spectra. As expected, biotinylated graphite retained streptavidin QDs but not anti-His-tag QDs, His-tagged graphite retained anti-His-tag QDs but not streptavidin QDs, and HA-tagged graphite retained anti-HA-tag fluorophores but not anti-His-tag QDs. See FIGS. 27-30 which show the selective attachment to surface-tagged graphite surfaces. FIG. 27 shows Raman and fluorescence spectra of biotin-functionalized graphite surfaces prior to binding protein treatment (orange), after incubation with streptavidin-coated quantum dots (red), and after incubation with His-tag antibody-coated quantum dots (olive). FIG. 28 shows Raman and fluorescence spectra of His-tag-functionalized surfaces prior to binding protein treatment (orange), after incubation with His-tag antibody-coated quantum dots (red), and after incubation with streptavidin-coated quantum dots (olive). FIG. 29 shows Raman and fluorescence spectra of HA-tag-functionalized surfaces prior to binding protein treatment (orange), after incubation with fluorophore-coated HA-tag antibodies (red), and after incubation with His-tag antibody-coated quantum dots (olive). Note the robust signals in cases of correctly paired surface tags and binding proteins, and absence of signal in mismatched samples. FIG. 30 shows label retention on His-tag-functionalized surface. Purple line shows the fluorescence spectrum of a mixed solution of 1:10 dilution streptavidin-coated quantum dots (585 nm, 2.12 eV) and 1:10 dilution His-tag antibody-coated quantum dots (655 nm, 1.89 eV). Upon incubation of mixture on His-tag-functionalized surface and repeated washing, only the 1.89 eV fluorescence peak corresponding to His-tag antibody-coated quantum dots remains (red). For comparison, Raman/fluorescence spectrum of bare His-tag-functionalized graphite surface is also shown (olive). Peak energies in Raman shift ($cm^{-1}$) and photon energy are shown for clarity. Excitation wavelength 532 nm. The corresponding type of graphite functionalization is indicated in italics. Notably, while the QDs exhibited symmetrical single emission peaks at their predicted wavelengths, the DyLight fluorophore had an additional minor peak around 615 nm/2.02 eV, consistent with its vendor-provided spectrum. In all cases, retention of the incompatible label was minimal, as evidenced by the background-level fluorescent spectra of such samples.

Electrode Functionality and Photoresponse of Surface-Tagged Graphite

Figure 32:
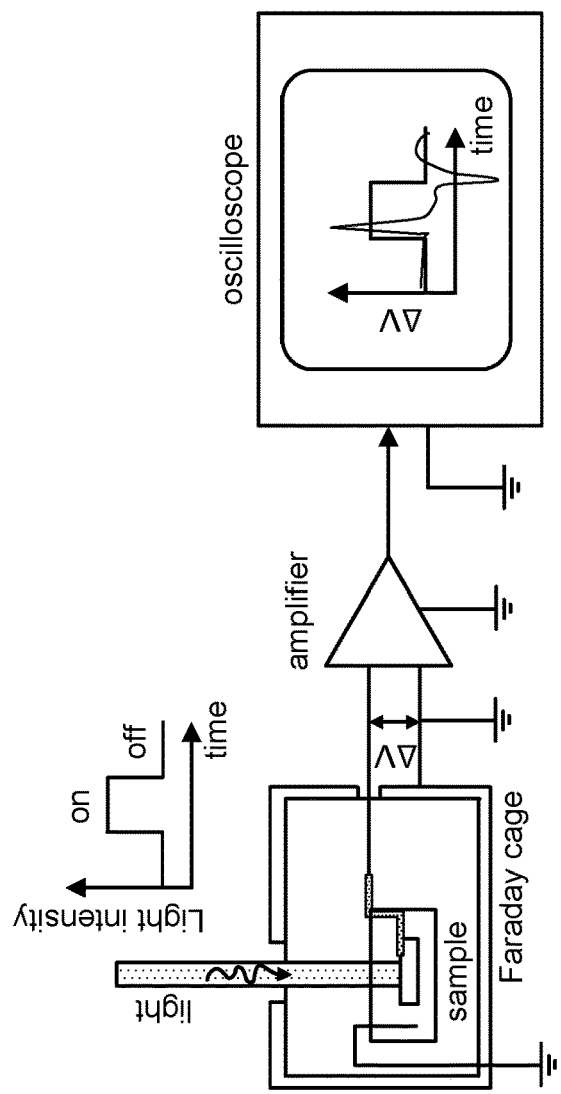
FIG. 32 shows the results of photoinduced electrical potential traces obtained with irradiation by a broad-spectrum quartz-halogen lamp for biotin-functionalized graphite incubated with streptavidin-coated quantum dots (red) and His-tag antibody-coated quantum dots (olive).
Figure 31:
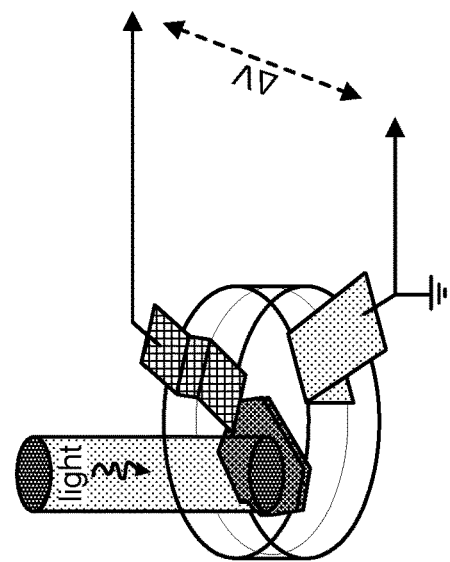
FIG. 31 is a schematic of the full electronic setup of the system in FIG. 30, including sample and leads in Faraday cage, amplifier, and oscilloscope. As shown, light is delivered as a pulse of uniform intensity, and the oscilloscope returns peaks at times when a voltage is induced and current flows, i.e. when light intensity changes. Signals were amplified with gain of 1000-2500.

Electrophysiologic measurements require signal acquisition systems that are sensitive enough to detect minute changes in electric fields near their surfaces with appropriate temporal resolution. To simulate local voltage fluctuations, we used surface-functionalized graphite complexed with the same fluorescent binders as above. Selectively-labeled surface-tagged graphite samples were placed into a cuvette filled with deionized (DI) water, with leads connected to an amplifier and oscilloscope, protected from external electromagnetic noise by a Faraday cage (FIGS. 31, 32). The cage had a small window to allow external illumination of the sample surface, with the leads outside the light path. Samples were not biased, and the photovoltaic signal between the leads induced by light illumination of the samples was amplified with a gain of 1000-2500. Samples were illuminated with flashes of 1-3 seconds in length.

Photoresponse was first assessed using a bright, broad-spectrum quartz-halogen lamp. Strong signals well above the noise level, in the tens of microvolts, were observed in samples incubated with fluorescent labels corresponding to the surface modifications (FIGS. 33-35). On the other hand, samples incubated with incompatible labels exhibited either undetectable or very weak (on the order of several microvolts) signals. The photoresponse of biotinylated and HA-tagged graphite in the absence of associated bright sources of fluorescence may reflect intrinsic photosensitivity of the attached molecules, in line with the strong fluorescence components in the Raman spectra of these materials. To further characterize the observed signal characteristics, the experiments were repeated using illumination with laser sources emitting at 532 nm, 633 nm, and 785 nm. As expected, photoresponse demonstrated wavelength dependence, confirming its reliance on the specific attachment of fluorescence sources. Biotinylated graphite with streptavidin QDs exhibited strong photoresponse to 532 nm excitation, above the QD emission wavelength of 585 nm, but no detectable signal with 633 nm excitation. His-tagged graphite with anti-His-tag QDs had strong photoresponse to 633 nm excitation, above the QD emission wavelength of 655 nm, but no response to 785 nm excitation. HA-tagged graphite with anti-HA-tag fluorophores also gave strong signal with 532 nm excitation, above the 576 nm fluorophore emission peak, but did not respond to 785 nm excitation.

What is claimed is:

1. A hybrid material comprising:
   a modified carbon support presenting internal molecular sites available for further attachment chemistry, wherein the internal molecular sites are not limited to the edges of the carbon structure; and
   one or more organic or inorganic entities attached to the internal molecular sites.

2. The hybrid material of claim 1 wherein the entity is a functional surface tag.

3. The hybrid material of claim 1 wherein the entity is a biotin or epitope tag.

4. The hybrid material of claim 3 wherein the epitope tag is selected from the group consisting of His and HA tags.

5. The hybrid material of claim 1 wherein the modified carbon is selected from the group consisting of graphene, graphite, fullerenes, and sp2-bonded carbon.

6. The hybrid material of claim 1 wherein the modified carbon is graphite.

7. The hybrid material of claim 1 wherein the modified carbon is graphene.

8. The hybrid material of claim 1 wherein the entity is selected from the group consisting of peptides, proteins, lipids, nucleic acids, antibodies and polymers.

9. A biocompatible electrode comprising the hybrid material of claim 1.

10. A method for forming a hybrid material comprising:
    modifying carbon to produce reactive internal molecular sites that are presented on the surface of the carbon and not limited to the edges of the carbon structure; and
    attaching an organic or inorganic entity to the reactive internal molecular sites.

11. The method of claim 10 wherein the reactive internal molecular sites are nitrile groups.

12. The method of claim 10 wherein the step of modifying carbon comprises:
    exposing the carbon to tetracyanoethylene oxide (TCNEO) to produce TCNEO-modified carbon; and
    reducing the TCNEO-modified carbon.

13. The method of claim 10 wherein the step of attaching an entity comprises solid phase synthesis of the organic or inorganic entity on the modified carbon.

14. The method of claim 10 wherein the step of attaching an entity comprises using covalent modification to attach the entity.

15. The method of claim 10 wherein the entity is a functional surface tag.

16. The method of claim 10 wherein the entity is a biotin or epitope tag.

17. The method of claim 16 wherein the epitope tag is selected from the group consisting of His and HA tags.

18. The method of claim 10 wherein the carbon is selected from the group consisting of graphene, graphite, fullerenes, and sp2-bonded carbon.

19. The method of claim 10 wherein the modified carbon is graphene or graphite.

20. The method of claim 1 wherein the entity is selected from the group consisting of peptides, proteins, lipids, nucleic acids, antibodies and polymers.

* * * * *